US00PP28717P3

(12) United States Plant Patent
Dobres et al.

(10) Patent No.: US PP28,717 P3
(45) Date of Patent: Nov. 28, 2017

(54) ***SALVIA* PLANT NAMED 'NOVASALPUR'**

(50) Latin Name: *Salvia hybrida*
Varietal Denomination: Novasalpur

(71) Applicant: CP DELAWARE, INC., Wilmington, DE (US)

(72) Inventors: Michael S. Dobres, San Javier (ES); Jessica D. Janes, Elkton, MD (US)

( * ) Notice: Subject to any disclaimer, the term of this patent is extended or adjusted under 35 U.S.C. 154(b) by 15 days.

(21) Appl. No.: 14/757,358

(22) Filed: Dec. 22, 2015

(65) Prior Publication Data

US 2017/0181354 P1 Jun. 22, 2017

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Buchanan Ingersoll & Rooney PC

(57) ABSTRACT

A new and distinct *Salvia* plant was formed by controlled breeding followed by selection. Over a long blooming season attractive purple blossoms are formed. The growth habit is well-branched and bushy. The blossoms are borne on sturdy stems. The plant can be readily asexually reproduced by the rooting of cuttings. The plant is well suited for providing attractive ornamentation in parks, gardens, public areas, and residential landscapes.

2 Drawing Sheets

Botanical/commercial classification: *Salvia hybrida/Salvia* Plant.

Varietal denomination: cv. Novasalpur.

SUMMARY OF THE INVENTION

The new cultivar of *Salvia hybrida* was created by artificial pollination carried out at West Grove, Pa., U.S.A., during January 2010 wherein two parents were crossed which previously had been studied in the hope that they would contribute desired characteristics. The female parent (i.e., seed parent) was the *Salvia hybrida* 'Ultra Violet' cultivar (U.S. Plant Pat. No. 21,411, granted Oct. 19, 2010). The male parent (i.e., pollen parent) was the 'San Carlos Festival' cultivar (non-patented).

The parentage of the new cultivar can be summarized as follows:

'Ultra Violet'×'San Carlos Festival'.

The seeds resulting from the pollination were collected during February 2010, were sown, and small plants were obtained which were acclimated to greenhouse conditions in May 2010 and were physically and biologically different from each other. Selective study resulted in the identification of a single plant of the new cultivar. A plant of the present invention was selected during July 2010 primarily in view of its abundance of attractive purple flowers, and well branched and sturdy stems. Had this new plant not been selected and preserved, it would have been lost to mankind.

The plant is a perennial that can be grown to advantage without protection in U.S.D.A. Hardiness Zone No. 6.

It was found that the new *Salvia* cultivar possesses the following combination of characteristics:

(a) displays a well-branched bushy growth habit with sturdy stems, (b) forms in abundance attractive purple blossoms, (c) displays hardiness to U.S.D.A. Hardiness Zone No. 6, and, (d) is well suited for providing attractive ornamentation.

The new cultivar of the present invention can be readily distinguished from other *Salvia* cultivars, such as the 'Ultra Violet' cultivar and the 'San Carlos Festival' cultivar. More specifically, the 'Ultra Violet' cultivar displays less sturdy branches and lesser hardiness, and the 'San Carlos Festival' cultivar displays dissimilar magenta blossoms. Additionally, compared to the 'Balmirdepur' variety, marketed under the name Salvia Mirage™ Deep Purple, the new variety displays flowers which are lighter purple in color and has an increased hardiness to zone 6. Also, the 'Bright Eyes' variety of U.S. Plant Pat. No. 22,491 displays red blooms with white eyes; the 'Golden Girl' variety of U.S. Plant Pat. No. 23,997 displays pale yellow blooms; and the 'Lemon Light' variety of U.S. Plant Pat. No. 24,105 displays bright yellow blooms.

The new cultivar well meets the needs of the horticultural industry and can be grown to advantage as attractive colorful ornamentation in parks, gardens, public areas, and residential landscapes.

The new cultivar has been asexually reproduced by the rooting of cuttings for several generations. Such asexual reproduction as performed at West Grove, Pa., U.S.A., has demonstrated that the characteristics of the new cultivar are firmly fixed and stable and are strictly transmissible from one generation to another. Accordingly, the new cultivar asexually reproduces in a true-to-type manner from one generation to another.

The new cultivar has been named 'Novasalpur', and will be marketed under the PURPLE ARCTIC BLAZE Trademark.

BRIEF DESCRIPITION OF THE PHOTOGRAPHS

The accompanying photographs show the new cultivar as nearly true as it is reasonably possible to make the same, in color illustrations of this character. The photographs were obtained during August 2015 at West Grove, Pa., U.S.A., and illustrate typical container grown four-year-old plants while being grown outdoors during August 2015.

DETAILED BOTANICAL DESCRIPTION

Figure 1:
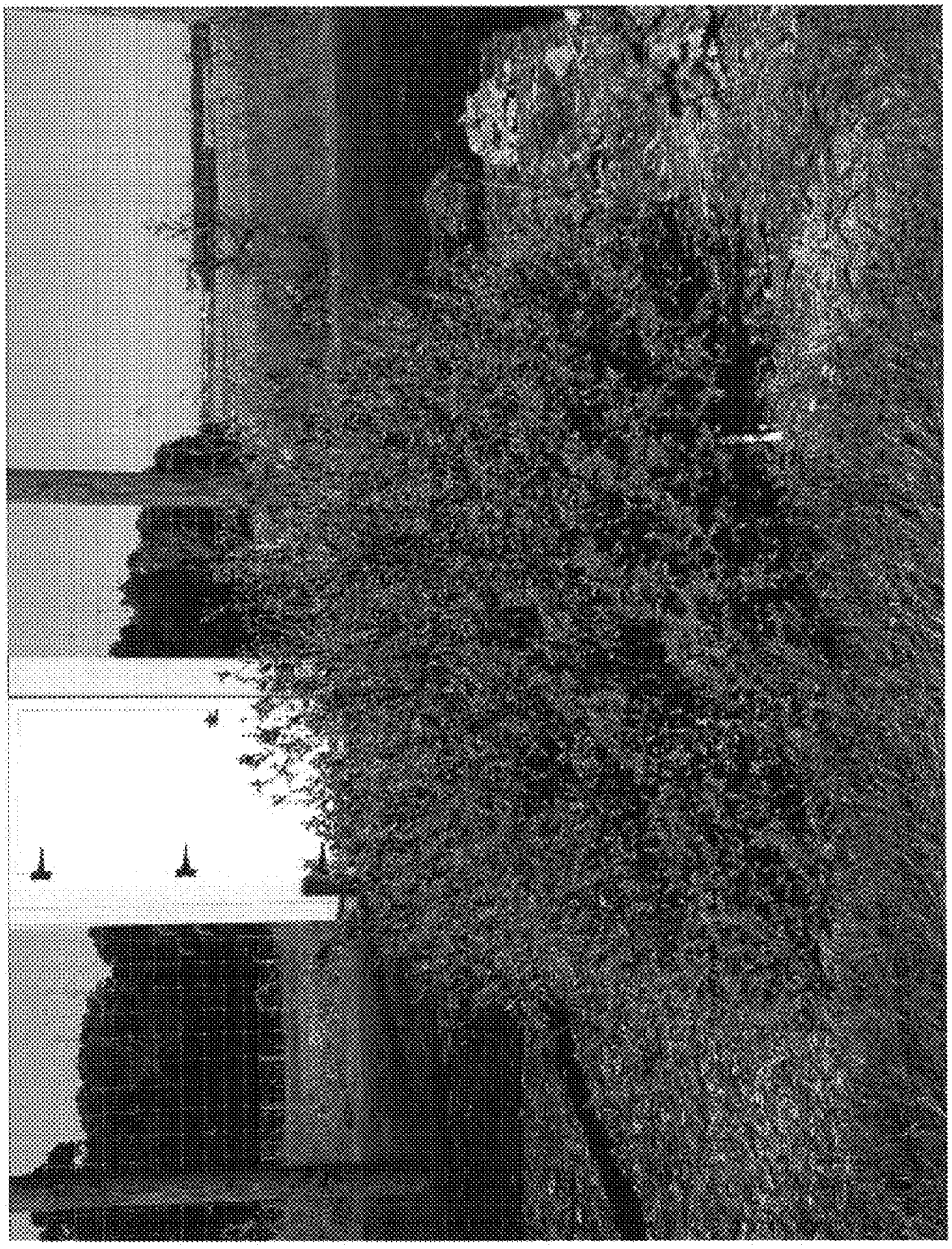
FIG. 1 illustrates the overall bushy growth habit of a flowering plant of the new cultivar.
Figure 2:
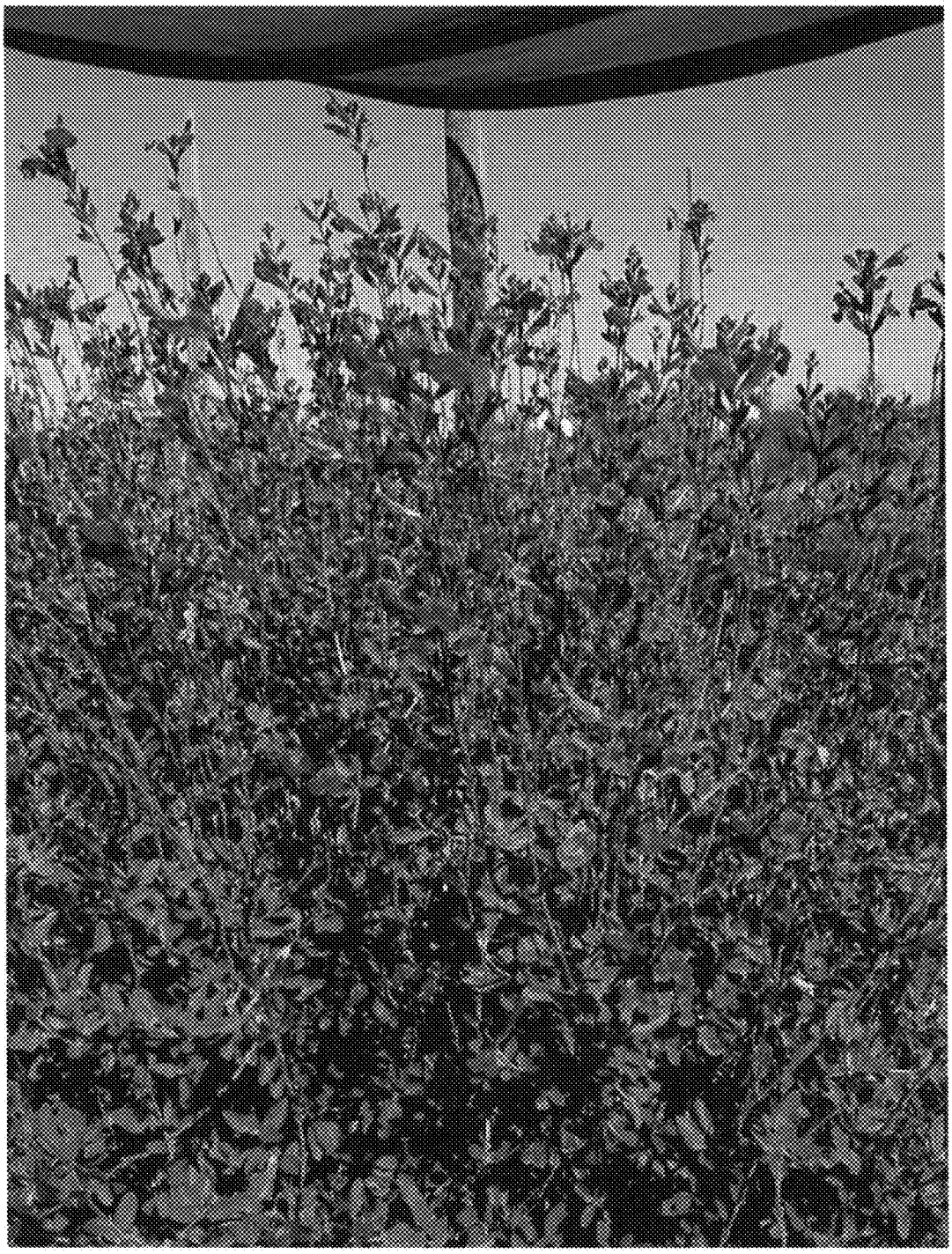
FIG. 2 illustrates a closer view of the attractive purple blossoms and foliage of the new cultivar.

The chart used in the identification of colors is that of The Royal Horticultural Society (R.H.S. Colour Chart) of London, England (1995). The description is based on the observation of typical specimens of the new cultivar at an age of approximately two years during August 2015 while growing outdoors in containers at West Grove, Pa., U.S.A.

Plant:

*Form*.—Bushy.

*Height*.—Commonly up to approximately 53 cm on average.

*Width*.—Commonly approximately 80 cm on average.

*Growth habit*.—Perennial in U.S.D.A. Hardiness Zone Nos. 6 to 11.

*Lateral branch number*.—21 on average per plant.

*Lateral branch color*.—Commonly near Brown Group N200B.

*Lateral branch texture*.—Commonly scabrous with older wood being more rugulose.

*Lateral branch length*.—Approximately 61 cm on average.

*Lateral branch diameter*.—Approximately 0.75 cm on average.

*Lateral branch internode length*.—Approximately 1.75-2.5 cm on average.

*Leaf arrangement*.—Opposite.

*Leaf configuration*.—Elliptic to oblong.

*Leaf length*.—Commonly approximately 4.5 cm on average.

*Leaf width*.—Commonly approximately 2 cm on average.

*Leaf margin*.—Repand.

*Leaf venation*.—Pinnipalmate pattern, and color is commonly near Green Group 137B.

*Leaf texture*.—Commonly slightly fleshy.

*Leaf blade color*.—Near Green Group 137B on the upper surface, and near Green Group 137C on the under surface.

*Leaf blade apex*.—Acute to obtusely rounded.

*Leaf blade base*.—Mainly obtuse.

*Scent*.—Leaves commonly display a tangy fruity scent when crushed.

*Petiole shape*.—Somewhat flattened.

*Petiole length*.—Variable and commonly approximately 1.8 cm on average.

*Petiole width*.—Commonly approximately 1 mm.

*Petiole color*.—Near Yellow-Green Group 144A.

Inflorescence:

*Type*.—Terminal raceme.

*Diameter*.—Commonly approximately 5 cm on average.

*Length*.—Commonly approximately 30 cm on average.

*Number*.—Commonly up to approximately 200 flowers per plant on average are in bloom at a given time.

*Configuration*.—Tubular, and two-lipped.

*Flower bud shape*.—Typically teardrop.

*Flower bud color*.—Commonly near Violet Group 83B.

*Flower bud length*.—Approximately 1.5 cm on average.

*Flower bud diameter*.—Approximately 0.4 cm on average on widest part.

*Pedicel length*.—Commonly approximately 4 mm on average.

*Pedicel width*.—Commonly approximately 1 mm on average.

*Pedicel color*.—Near Green Group 143D and overlaid with Brown Group 200A.

*Pedicel pubescence*.—Present, with pedicel being puberulent.

*Calyx shape*.—Broadly campanulate and flared towards the apex.

*Calyx rib number*.—Commonly 15 on average and longitudinally disposed.

*Calyx length*.—Commonly approximately 1.3 cm on average.

*Calyx width*.—Commonly up to 6 mm.

*Calyx texture*.—Glandular and puberulent on the upper and under surfaces.

*Calyx color*.—On the upper lobe near Green Group 138A overlaid with Brown Group 200A towards the apex, and on the lower lobes near Green Group 138B overlaid with Brown Group 200A towards the apex.

*Calyx lobe number*.—3.

*Calyx upper lobe number*.—1.

*Calyx upper lobe shape*.—Acute.

*Calyx upper lobe length*.—Commonly approximately 1.2 cm on average.

*Calyx upper lobe width*.—Commonly approximately 6 mm in width on average.

*Calyx lower lobe number*.—2.

*Calyx lower lobe shape*.—Acute.

*Calyx lower lobe length*.—Commonly approximately 1.2 cm on average.

*Calyx lower lobe width*.—Commonly approximately 4 mm on average.

*Corolla shape*.—Tubular proximally to two-lipped distally.

*Corolla length*.—Commonly approximately 2.8 cm on average.

*Corolla color*.—The base commonly is near White Group 155C, the tube is near Purple-Violet Group 80A, and the lower lip is near Purple-Violet Group 81A.

*Corolla tube length*.—Approximately 1.8 cm on average.

*Corolla tube depth*.—Approximately 6 mm on average.

*Corolla tube lip number*.—3.

*Corolla upper lip number*.—1.

*Corolla upper lip shape*.—Hood-like.

*Corolla upper lip length*.—Commonly approximately 8 mm average.

*Corolla lower lip length*.—2, suborbicular.

*Corolla lower lip shape*.—Banner-like, and extended downward.

*Corolla lower lip outline*.—Obovate.

*Corolla lower lip length*.—Commonly approximately 1.2 cm on average.

*Corolla lower lip diameter at tip*.—Approximately 1.1 cm on average.

*Style length*.—Approximately 2.5 cm on average.

*Style width*.—Commonly less than 1 mm.

*Style attachment site*.—At four-lobed ovary between lobes.

*Ovary*.—Approximately 5 mm in length, approximately 1 mm in diameter, and near Yellow-Green Group 151B in coloration.

*Stamen number*.—1.

*Stamen shape*.—Seesaw-like.

*Filament length*.—Approximately 1.1 cm on average.

*Connective length*.—Approximately 4 mm on average.

*Anther length*.—Approximately 2 mm on average.

*Anther diameter*.—Less than 1 mm.

*Anther color*.—Near Greyed-Orange Group 163A.

*Anther attachment site*.—At outer end of the connective.

*Pollen*.—Abundant.

*Seed*.—Commonly oval in shape, and commonly 1-4 seeds per pod on average.

Development:

*Vegetation*.—Well-branched with sturdy stems.

*Blooming*.—Displays a strong propensity to reblossom from spring through fall to rebloom.

*Winter hardiness*.—The plant is a perennial that can be grown in U.S.D.A. Hardiness Zone Nos. 6 to 11.

*Disease resistance*.—Typical for *Salvia* with no particular sensitivity to disease having been encountered during observations to date.

*Number of days to initiate roots*.—Approximately 10-14 days on average.

*Number of days to produce a rooted cutting*.—Approximately 28-35 days on average.

The new 'Novasalpur' cultivar has not been observed under all possible environmental conditions. Accordingly, it is possible that the phenotypic expression may vary somewhat with changes in light intensity and duration, cultural practices, and other environmental conditions.

We claim:

1. A new and distinct *Salvia* plant characterized by the following combination of characteristics:

(a) displays a well-branched bushy growth habit with sturdy stems, (b) forms in abundance attractive purple blossoms, (c) displays hardiness to U.S.D.A. Hardiness Zone No. 6, and (d) is well suited for providing attractive ornamentation; substantially as illustrated and described.

* * * * *